(12) United States Patent
Davis, II et al.

(10) Patent No.: US 9,987,046 B2
(45) Date of Patent: Jun. 5, 2018

(54) PEDICLE SCREW ASSEMBLY

(71) Applicants: Charles William Davis, II, Kingsville, MD (US); Krista Bayne, Catonsville, MD (US)

(72) Inventors: Charles William Davis, II, Kingsville, MD (US); Krista Bayne, Catonsville, MD (US)

(*) Notice: Subject to any disclaimer, the term of this patent is extended or adjusted under 35 U.S.C. 154(b) by 0 days. days.

(21) Appl. No.: 15/374,814

(22) Filed: Dec. 9, 2016

(65) Prior Publication Data
US 2017/0164982 A1    Jun. 15, 2017

Related U.S. Application Data

(60) Provisional application No. 62/265,439, filed on Dec. 10, 2015.

(51) Int. Cl.
*A61B 17/70* (2006.01)

(52) U.S. Cl.
CPC ...... *A61B 17/7037* (2013.01); *A61B 17/7032* (2013.01); *A61F 2310/00029* (2013.01); *A61F 2310/00059* (2013.01)

(58) Field of Classification Search
CPC .............. A61B 17/704; A61B 17/7032; A61B 17/7034
See application file for complete search history.

(56) References Cited

U.S. PATENT DOCUMENTS

| 5,733,286 | A | 3/1998 | Errico et al. |
|---|---|---|---|
| 5,800,435 | A | 9/1998 | Errico et al. |
| 6,302,888 | B1 | 10/2001 | Mellinger et al. |
| 6,565,566 | B1* | 5/2003 | Wagner .............. A61B 17/7002 606/267 |
| 6,660,005 | B2* | 12/2003 | Toyama ............. A61B 17/7032 606/269 |
| 7,479,156 | B2 | 1/2009 | Lourdel et al. |
| 7,686,833 | B1 | 3/2010 | Muhanna et al. |
| 7,875,065 | B2 | 1/2011 | Jackson |
| 2003/0100904 | A1* | 5/2003 | Biedermann ...... A61B 17/7032 606/272 |
| 2005/0192571 | A1* | 9/2005 | Abdelgany ........ A61B 17/7037 411/427 |
| 2006/0036244 | A1* | 2/2006 | Spitler ................... A61B 5/103 74/1 R |

(Continued)

OTHER PUBLICATIONS

Spine Surgery Instrumentation, http://www.infospine.net/treatment-spine-surgery-instrumentation.html, The Anand Spine Group, date accessed: Dec. 6, 2016.

*Primary Examiner* — Julianna N Harvey
(74) *Attorney, Agent, or Firm* — Andrews Kurth Kenyon LLP

(57) ABSTRACT

A top-loading pedicle screw system for correcting a misalignment of the spinal column of a patient. The top-loading pedicle screw assembly comprises a screw having a threaded shaft for affixation the assembly to a vertebral pedicle. The screw has a shank top forming an internal curved socket. A head is positioned within the socket to move in a multi-axial relationship thereto. A through bore is formed in the head to receive a rod that joins two or more pedicle screw assemblies to the spinal column of a patient. A locking element is inserted into the head to lock the rod to the head while also locking the head to the shank top of the screw.

22 Claims, 10 Drawing Sheets

(56) References Cited

U.S. PATENT DOCUMENTS

2007/0161994 A1* 7/2007 Lowery .............. A61B 17/7032
                                                                606/86 A
2008/0119858 A1   5/2008 Potash
2009/0312804 A1  12/2009 Gamache et al.

\* cited by examiner

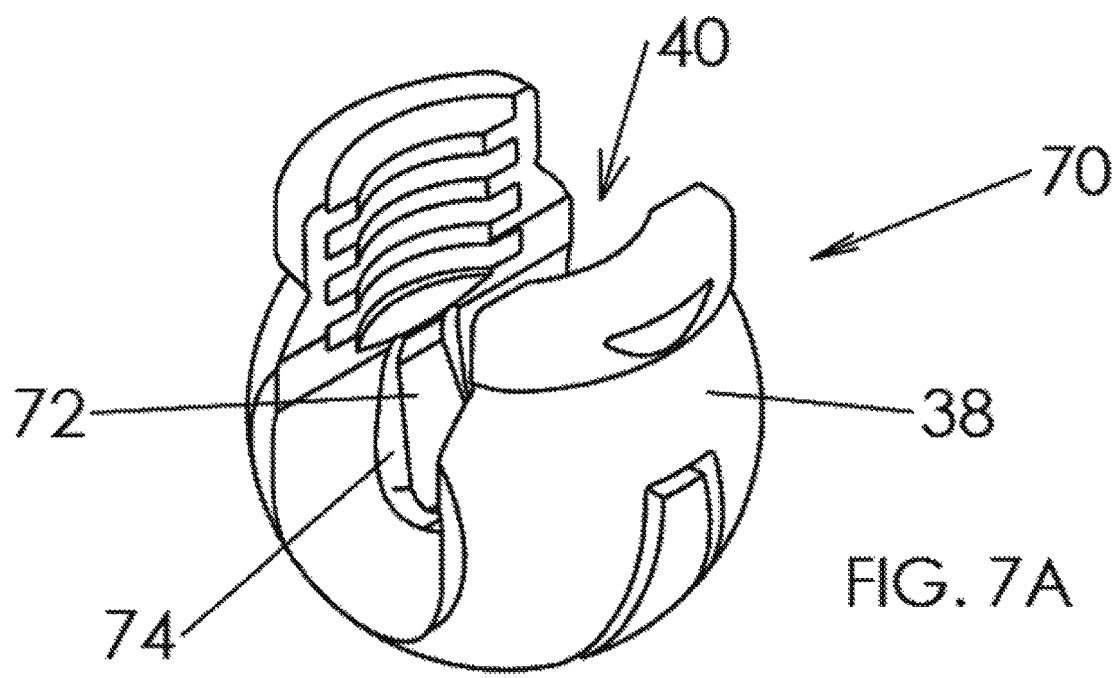

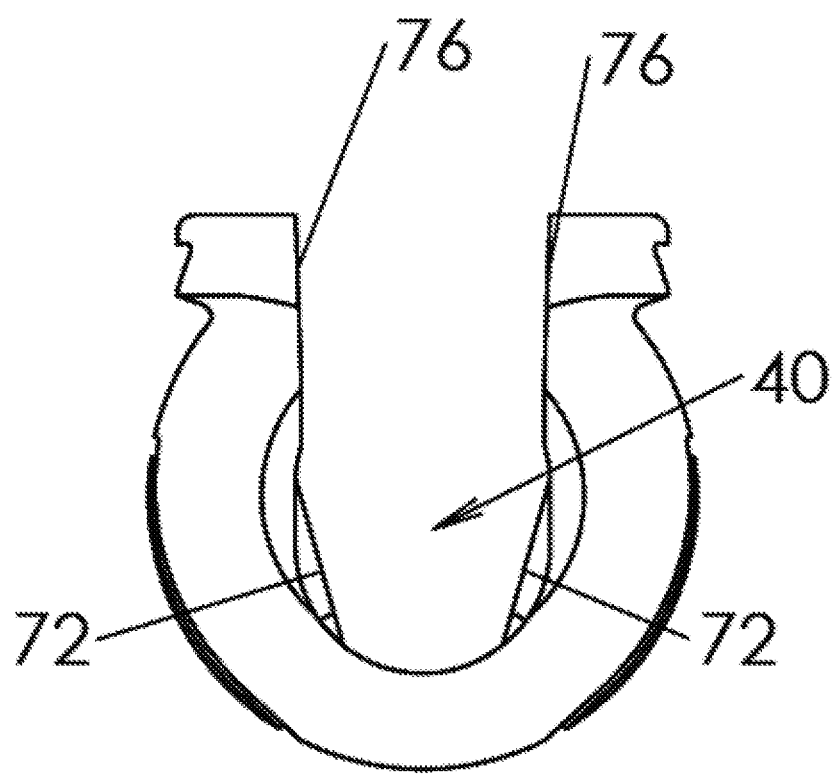

PEDICLE SCREW ASSEMBLY

This application claims priority to U.S. Provisional Patent Application No. 62/265,439, filed on Dec. 10, 2015. The entirety of the aforementioned application is incorporated herein by reference. The present disclosure relates to the field of orthopedic implements, and, more particularly, to a top-loading pedicle screw assembly adapted to be screwed into two or more vertebral pedicles for affixing a rod or other joining implement to the vertebral pedicles.

TECHNICAL FIELD

Background

Pedicle screw assemblies are well known devices and are often used to fasten an orthopedic implement, such as a solid bar, to two or more vertebrae to hold the vertebrae into a desired orientation.

A common design for a pedicle screw system is to have a screw shank top that is shaped as a spherical top and there is a head or socket that is attached to the spherical screw shank top to move poly-axially therewith. As such, the screw shank top is normally spherical with the head fitting over that spherical shaped shank top to allow movement there between.

One problem, however, with such a design is that the rod that extends between two or more pedicle screw systems is displaced away from the spinal column whereas it would be preferable for the rod to be positioned as close to the spinal column as possible. In addition, with the prior art systems, there are insertional complications since the threaded shank portion can become misaligned during the insertion process. For example, the threaded shank portion may become misaligned from the head which is held by instrumentation during the insertion process.

Accordingly, it would be advantageous to have a specially designed pedicle screw assembly where the rod joining two or more pedicle screw systems can be positioned close to the spinal column and also a system that can be readily installed to the spinal column in a positive and stable alignment manner. It would be further advantageous to have a pedicle screw assembly having the ability to allow poly-axial motion while having a direct connection to the alignment features that are necessary for screw insertion into the spinal column.

BRIEF SUMMARY OF THE DISCLOSURE

The present disclosure therefore, improves upon the features of the existing pedicle screw systems and includes a screw having a distal end with a threaded shaft and a proximal screw shank top that forms a socket for a head that is interfitted into that socket. As such, the insertion cannot become misaligned since the screw shank, which is held for alignment during insertion, is integral with the threaded shaft and, therefore, there is no movement between the screw shank top and the threaded shaft of the screw, yet the poly-axial motion is maintained. In addition, with the present disclosure, the location of the rod, as finally installed, is positioned closer to the spinal column than with the prior art systems. In addition, the present disclosure positions the rod at the center of, or close to the center of, the socket head interface.

As such, with the present disclosure, the distal or threaded end of the threaded shaft is pointed and is screwed into the vertebral pedicle. The proximal end is integral with the threaded shaft and can easily be manipulated to carry out the screwing of the screw into the vertebral pedicle. In one aspect, the screw shank top has two flat outer surfaces to facilitate the grasping and rotating of the screw in order to screw it into the vertebral pedicle of the patient.

The interior surface of the shank top of the screw is a specially formed curved surface, such as a spherical configuration, to form a socket that receives the head that interfits into the interior socket of the shank top of the screw. The head has a lateral through bore to position and hold the rod as it passes through the head. The shape of the head is such as to conform to the interior surface of the shank top of the screw to allow the poly-axial movement between the head and the screw shank top. In one aspect, the exterior surface of the head and the interior surface of the shank top of the screw are both spherical.

A locking element is introduced into the head so as to lock the head within the socket of the screw shank top. In one aspect, the locking element can be a set screw that is introduced into the head to expand the exterior surface of the head to firmly lock that head to the shank top of the screw so as to lock the rod in its desired position interconnecting to two or more vertebral pedicles.

Other features of the present pedicle screw assembly will become more apparent in light of the following detailed description and as illustrated in the accompanying drawings.

BRIEF DESCRIPTION OF THE DRAWINGS

FIG. 7A shows another design of the head, according to one aspect of this disclosure.

FIG. 7C shows a cross-sectional view of the head 70 taken along the A-A line in FIG. 7B, according to one aspect of this disclosure.

DETAILED DESCRIPTION

Figure 1:
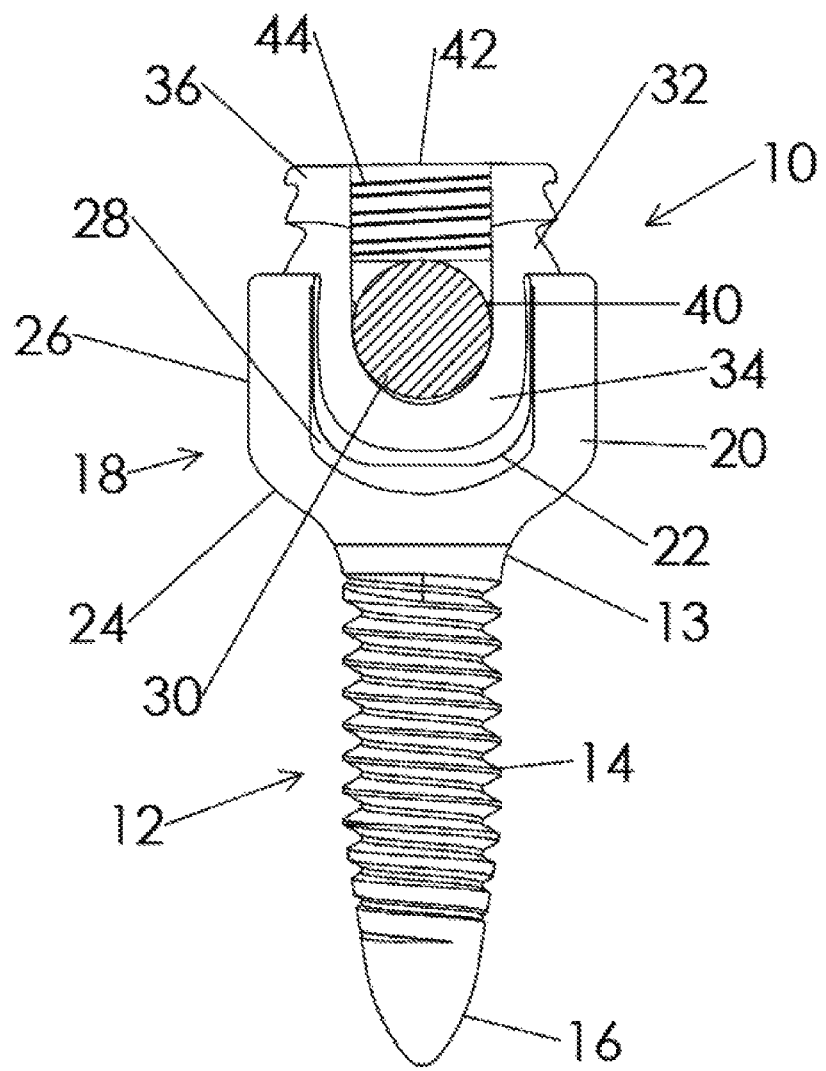
FIG. 1 is a side view, partly in cross section, illustrating the pedicle screw assembly, according to one aspect of this disclosure.

In FIG. 1, there is shown a side view illustrating the pedicle screw system 10 of the present disclosure. As can be seen in FIG. 1, the pedicle screw system 10 comprises a screw 12 having a threaded shaft 14 ending in a pointed distal end 16 that is adapted to be screwed into a pedicle of a patient's spine. The screw 12 is preferably made of titanium; however, other materials could be used, such as stainless steel or cobalt chrome. Alternatively, the screw 12 can be made by powder metallurgy methods using powder that is sintered to form the finished form. In such case, the material may be stainless steel.

At the proximal end 18 of the screw 12, there is a shank top 20 that is specially designed in accordance with the present disclosure. As can be seen, the shank top 20 has an interior socket 22 forming by its interior spherically shaped surface and an exterior surface 24 having oppositely disposed flat surfaces 26 to enable the physician to use a tool to grasp the shank top 20 to screw the screw 12 into the vertebral pedicle of the patient. The flat surfaces 26 are shown in FIG. 1 in one location, however, it may be seen that the flat surfaces 26 may be moved 90 degrees or at some intermediate offset.

There are lateral openings 28 (only one is shown in FIG. 1) that pass through the shank top 20 and are provided to make space for the addition of a rod 30 that passes through the lateral openings 28 so that the rod can be poly-axially affixed to the pedicle screw assembly 10 and connect the pedicle screw assembly 10 in FIG. 1 to at least another, adjacent pedicle screw assembly in creating some stability to the spinal column of the patient. In one aspect, the rod 30 may inserted into a through bore 40 (discussed in more detail below). In one aspect, the rod 30 may be lowered into the through bore 40 by passing the rod 30 through the threaded bore 42 (discussed in more detail below). Therefore, in one aspect of this disclosure, the pedicle screw system 10 may be a top-loaded pedicle screw.

Interfitted into the shank top 20 is a head 32 that is comprised of a main body 34 that is generally arcuate and has an outer flange 36. As can be seen, the outer surface 38 (shown in FIG. 4) of the main body 34 is shaped to be compatible with the interior surface 22 of the shank top 20 so that the head 32 can move with a poly-axial motion with respect to the shank top 20 and, correspondingly, to the screw 12. This is one aspect in which this disclosure differs from what is taught in the prior art. As discussed above, prior art systems have a screw that rotates about the shank top. However, in this aspect of this disclosure, the shank top 20 and the screw 12 are in a fixed relationship. Rather, it is the interfitted head 32 that enables poly-axial motion. Again, the head 32, like the screw 12, can be a sintered material such as cobalt/chrome.

In one aspect as illustrated in the figures, the outer surface 38 of the main body 34 is spherical as is the interior surface of the shank top 20 so as to accommodate the poly-axial movement. One of ordinary skill in the art would readily recognize that shapes other than spherical may be used to accommodate the poly-axial movement.

The head 32 has the through bore 40 to allow the rod 30 to pass therethrough for the purpose previously described. The through bore 40 is oriented about normal to the main longitudinal axis of the screw 12. Head 32 also includes a threaded bore 42 having a main axis generally parallel to or even coaxial with the main longitudinal axis of the screw 12. The threaded bore 42 includes threads 44 leading up to the outer flange 36. In one aspect of this disclosure, the threads 44 may be dovetail threaded. When the threads 44 are dovetail threaded, it may mate with a locking element (described in more detail below) which may also be dovetail threaded.

A locking element is thus used to lock the rod 30 to the head 32 such that the rod 30 moves along with the head 32 as the latter is poly-axially moved with respect to the shank top 20. In one aspect of the present disclosure, the locking element is a set screw 46 (shown in FIG. 4) having threads 48 that mesh with the threaded bore 42 so that the set screw 46 can be screwed into the threaded bore 42. While a set screw 46 is certainly feasible as the locking element, it can be seen that other devices can be used in place of the set screw to lock the rod 30 to the head 32. As alluded to above, in one aspect of this disclosure, the locking element may be dovetail threaded. When the locking element is dovetail threaded, it may mate with a dovetail threaded thread 44.

The pedicle screw system 10 may include a base 13. In one aspect, the base 13 may have four flat surfaces such that a cross-section of the base 13 may be rectangular. In another aspect, the base 13 may be cylindrical such that the cross-section of the base 13 may be circular. One of ordinary skill in the art would readily recognize that other shapes of the base 13 may be used.

Figure 2:
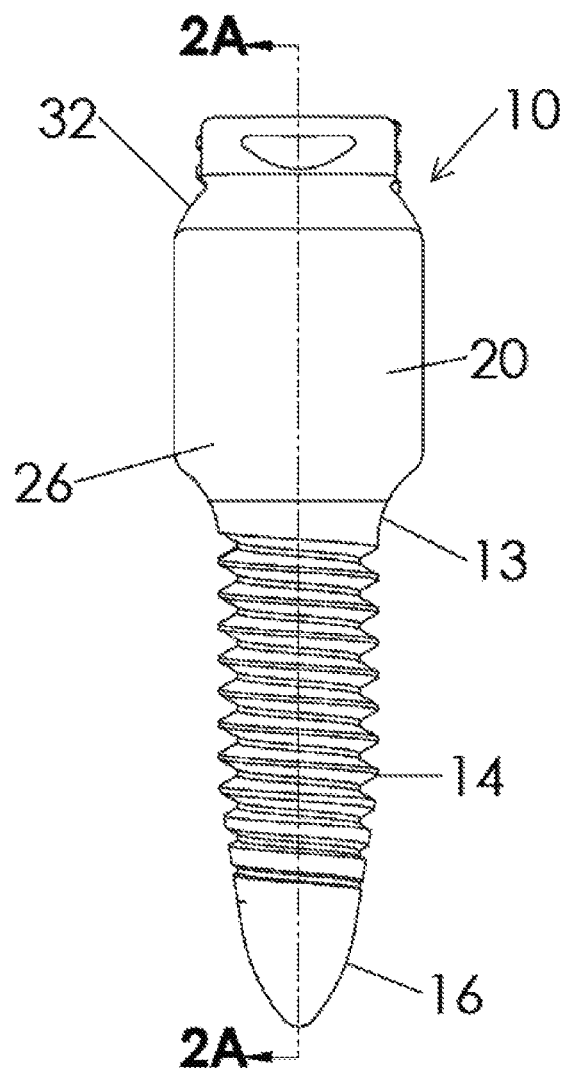
FIG. 2 is a front view of the pedicle screw assembly of FIG. 1, according to one aspect of this disclosure.

Turning now to FIG. 2, there is shown a front view of the pedicle screw system 10 of the present disclosure. FIG. 2 illustrates one of the flat surfaces 26 of the shank top 20 that facilitate the function of screwing the screw 12 into the vertebral pedicle of a patient and, again the flat surfaces 26 are oriented in one position in FIG. 2; however, it can be seen that the flat surfaces may be in other orientations while maintaining their separation at 180 degrees.

Figure 2A:
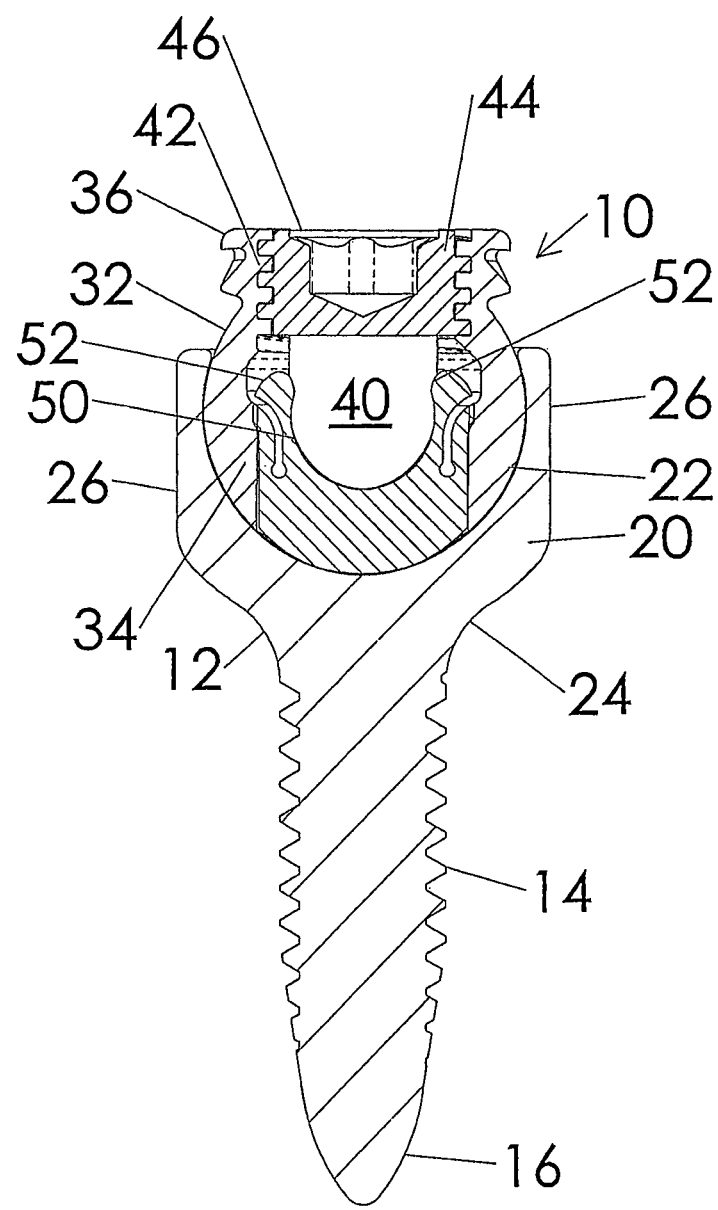
FIG. 2A is a side cross sectional view of the pedicle screw assembly of FIG. 1 taken along the line 2A-2A of FIG. 2, according to one aspect of this disclosure.

FIG. 2A is a cross-sectional view of the present pedicle screw system 10 taken along the line 2A-2A of FIG. 2 and illustrates an optional feature of the present disclosure. That optional feature is a clip 50 that can be positioned within the interior of the head 32. The clip 50 can be a relatively flexible member that allows the physician to simply snap the rod 30 into the head 32 to temporarily hold the rod 30 in position while other activities are being conducted during the surgery.

In one aspect as illustrated in FIG. 2A, the clip 50 can be seen to be U-shaped with a pair of ends 52 facing the set screw 46 forming an opening 54. As such the insertion of the rod 30 (shown in FIG. 1) flexes the ends 52 outwardly so that the rod 30 passes through the opening 54 in a snap-in manner to seat the rod 30 within the head 32. Accordingly, the presence of the clip 50 is a convenience to the physician in carrying out the overall operation. The clip 50 may be designed so it also contacts the inner surface of the shank top 20 (shown spherically), thus causing a friction contact when the set screw 46 engages the rod 30. In one aspect of this disclosure, an outer edge of the clip 50 may have a shape similar to gear teeth around the edge of the clip 50. In this aspect, the gear teeth may be in contact with the shank top 20.

Figure 3:
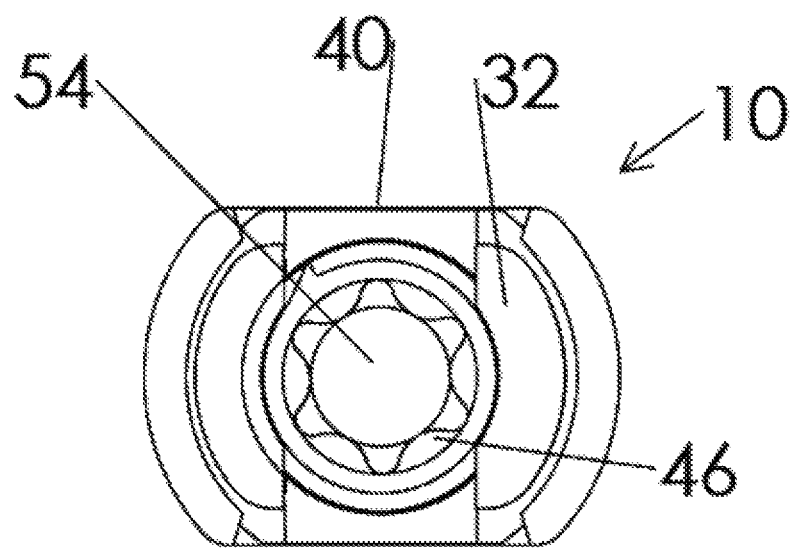
FIG. 3 is as top view of the pedicle screw assembly of FIG. 1, according to one aspect of this disclosure.

Turning then to FIG. 3, there is shown a top view of the pedicle screw system 10 of the present disclosure and illustrating, again, the flat surfaces 26 along with the upper surface of the set screw 46 with an indentation 54 that is shaped to receive a tool manipulated by a physician to screw the set screw 46 into the head 32.

Figure 4:
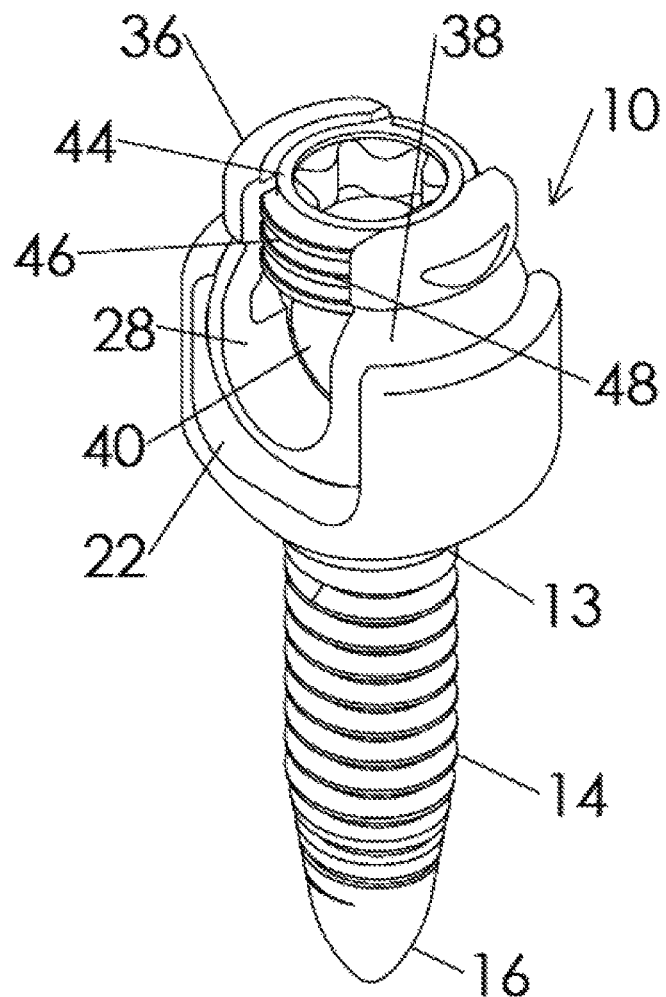
FIG. 4 is a perspective view of the pedicle screw assembly of FIG. 1, according to one aspect of this disclosure

Turning to FIG. 4, taken along with FIG. 1, there is a perspective view of the pedicle screw system 10 of the present disclosure and, as can be seen, the set screw 46 has been screwed into the head 32. The progress of the set screw 46 and its insertion into the head 32 may serve two purposes. First, the insertion of the set screw 46 forcefully presses against the rod 30 to stabilize and hold the rod 30 firmly affixed to the head 32 and secondly, the insertion of the set screw 46 serves to expand the threaded bore 42 to, in turn, expand the outer surface 38 of the main body 34 of the head 32 so that the outer surface 38 forcefully engages the interior socket 22 of the shank top 20, thus locking the head 32 into position within the shank top 20. In addition, the force drives the rod 30 into the clip 50, if present, causing additional locking between the head 32 and the shank top 20.

Accordingly, the dimensions of the set screw 46 and threaded bore 42 are predetermined so that the expansion of the main body 34 by the insertion of the set screw 46 into that threaded bore 42 is sufficient to engage and lock the head 32 within the shank top 20.

As such, the pedicle screw of the present disclosure is modular, that is, the head is readily and easily disconnected from the socket without damage to any of the components. As such, the connection is permanent enough to perform surgical expectations but simple enough to take apart wherein the pieces or components could be interchanged in the operating room. The head 32 cannot be disconnected with the rod 30 in place.

Figure 5:
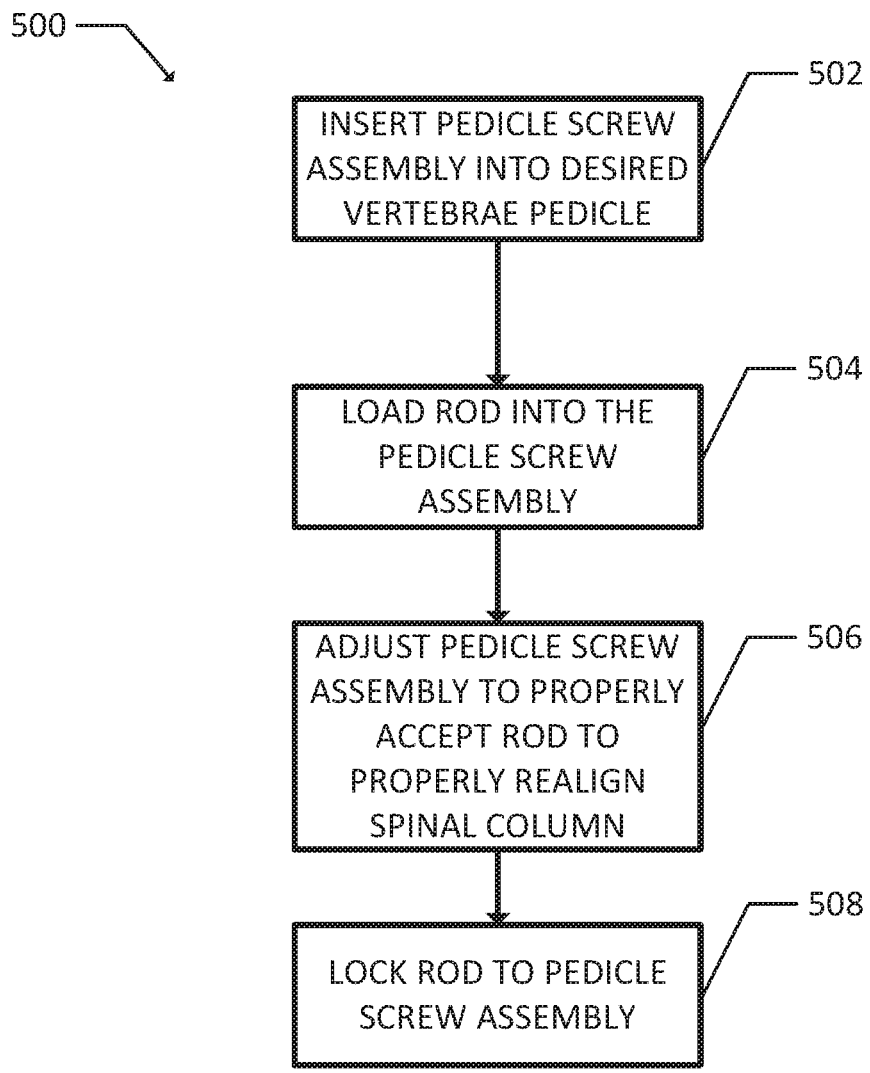
FIG. 5 shows a method for inserting the pedicle screw assembly into a vertebrae, according to one aspect of this disclosure.

FIG. 5 shows a method 500 for inserting the pedicle screw 10 into a vertebrae, according to one aspect of this disclosure. The method 500 may begin at block 502. At block 502, the pedicle screw 10 may be inserted into a desired vertebrae pedicle. For example, the desired vertebrae pedicle may be a vertebrae pedicle needing to be aligned. After block 502 is completed, the method 500 may proceed to block 504.

At block 504, the rod 30 may be loaded into the through bore 40 of the pedicle screw 10. The rod 30 may be inserted in any suitable manner. For example, in one aspect of this disclosure, the rod 30 may be top loaded into the pedicle screw 10. In this aspect, the rod 30 may be lowered into the through bore through the threaded bore 42. In another aspect, the rod 30 may be inserted directly into the through bore, skipping the open channel. After block 504 is completed, the method 500 may proceed to block 506.

At block 506, the pedicle screw 10 may be adjusted to properly accept the rod 30. For example, the curvature of the rod 30 may require that the head of the pedicle screw 10 be oriented in a certain manner to properly align the spine. One of ordinary skill in the art would readily recognize that other adjustments may be needed to properly accept the rod 30 to align the spine. After block 506 is complete, the method 500 may proceed to block 508.

At block 508, the rod 30 may be locked to the pedicle screw 10. For example, the set screw 46 may be inserted into the threaded bore 42. The set screw 46 may apply a downward force to the rod 30, which in turn may apply an outward force to the head 32. The head 32 may then press against the shank top 20, locking the head 32 in place. After block 508 is completed, the method 500 may end.

One of ordinary skill in the art would readily recognize that method 500 may be used with any number of pedicle screws 10. For example, a plurality of screws may be used to hold the 30 to properly align the spine.

Figure 6:
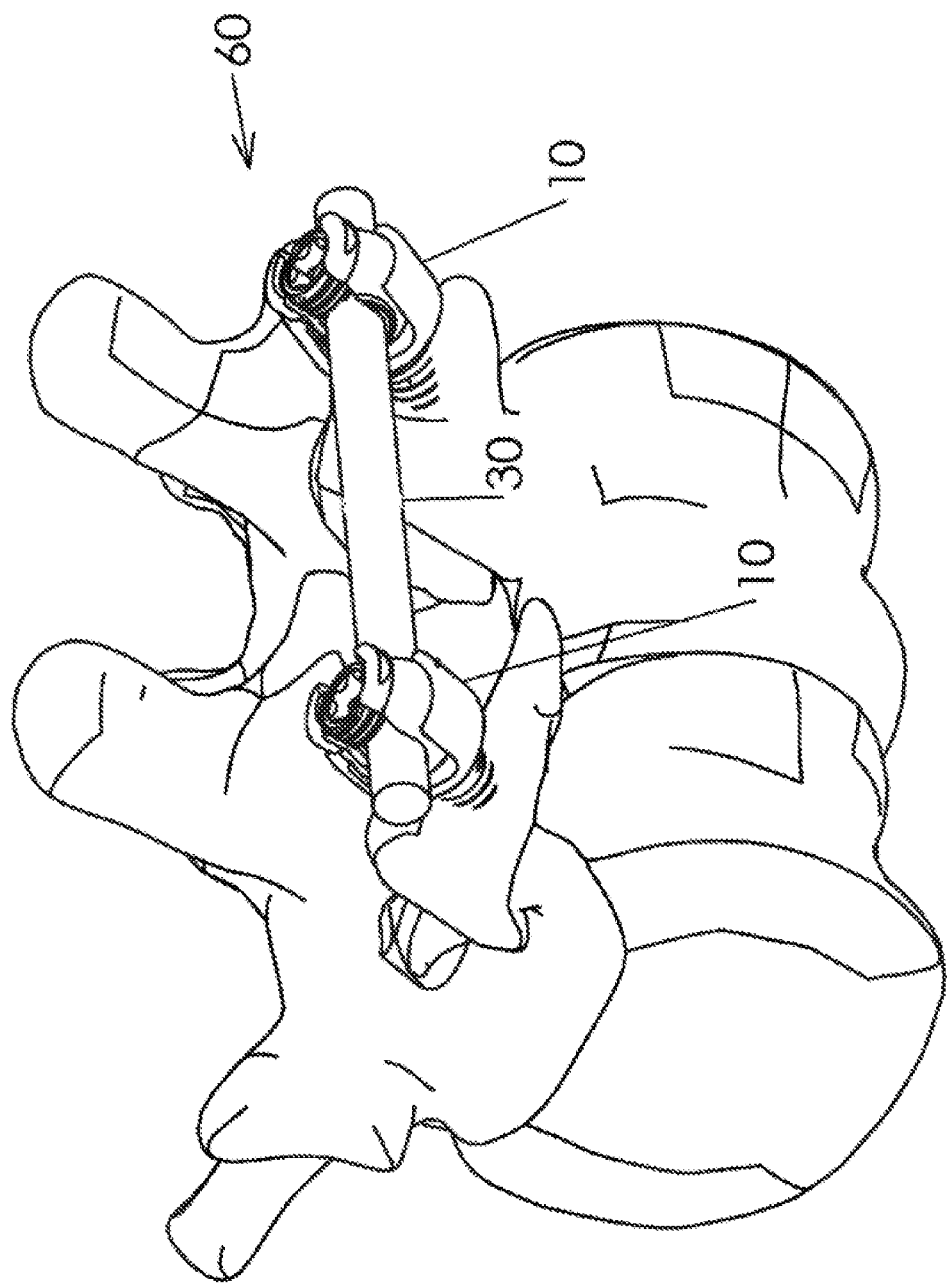
FIG. 6 shows a perspective view of two consecutive vertebrae and two pedicle screw assemblies, according to one aspect of this disclosure.

FIG. 6 shows a perspective view 60 of two consecutive vertebrae and two pedicle screw assemblies 10, according to one aspect of this disclosure. As shown in FIG. 6, each of the vertebrae has a pedicle screw assembly 10 coupled to it. After each pedicle screw 10 is coupled to the respective vertebrae, the rod 30 may be inserted into the head 32 for each pedicle screw assembly 10. The rod 30 may be inserted into the heads by lowering the rod through the opening. The rod 30 may serve to align the vertebrae. After the rod 30 has been inserted into the heads 32, a locking element may be inserted into the threaded bore 42, which may lock both pedicle screw assemblies 10.

FIG. 7A shows another design of a head 70, according to one aspect of this disclosure. In this aspect, the head 70 may include at least one angled surface 72. In one aspect of this disclosure, the head 70 may include two angled surfaces 72 facing the through bore 40. The head 70 may also include a slot 74. The slot 74 may be formed in the inner surface of the head 70. Therefore, when the set screw 46, for example, is tightened, the set screw 46 not only spreads the outer surface 38 of the head 70, via the rod 30, to lock it, but the slot 74 may spread even further to assist in the locking. In this aspect, the head 70 may not include a clip 50.

Figure 7B:
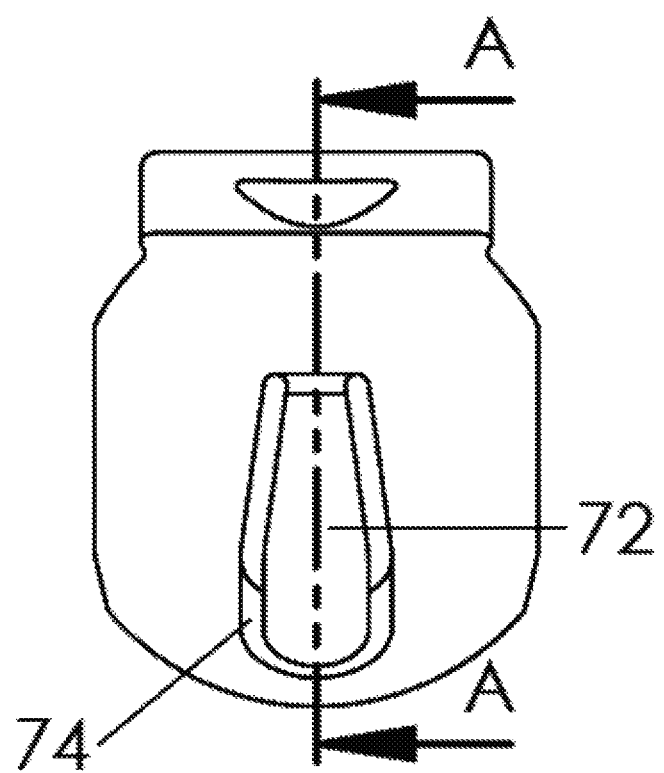
FIG. 7B shows a side view of the head 70, according to one aspect of this disclosure.

FIG. 7B shows a side view of the head 70, according to one aspect of this disclosure. As shown in FIG. 7A, the slot 74 is center aligned in the head 70. One of ordinary skill in the art would readily recognize that the slot 74 may be located in other positions in the head 70.

FIG. 7C shows a cross-sectional view of the head 70 taken along the A-A line in FIG. 7B, according to one aspect of this disclosure. This cross-sectional view of the head 70 shows two angled surfaces 72. In this aspect, the two angled surfaces 72 are opposite each other. However, one of ordinary skill in the art would readily recognize that other relative positions of the two angled surfaces 72 may be possible. Additionally, one of ordinary skill in the art would also recognize that any number of angled surfaces 72 may be used.

While the present disclosure has been set forth in terms of a specific aspect or aspects, it will be understood that the pedicle screw assembly herein disclosed may be modified or altered by those skilled in the art to other configurations. Accordingly, the disclosure is to be broadly construed and limited only by the scope and spirit of the claims appended hereto.

What is claimed is:

1. A top-loading pedicle screw assembly comprising:
   a screw having a threaded shaft for affixation to a vertebral pedicle,
   a shank top permanently fixed to the screw forming an internal curved socket and including lateral openings,
   a head having a through bore therethrough, an external curved surface movably fitted within the internal curved socket of the shank top, and an open channel formed therein, the head being configured to allow the rod to be top-loaded into the through bore and the lateral openings of the shank top, and
   a locking element adapted to be inserted into the open channel to lock the head to the shank top of the screw.

2. The top-loading pedicle screw assembly as defined in claim 1, wherein one or both of the screw or head is comprised of a sintered metal.

3. The top-loading pedicle screw assembly as defined in claim 2, wherein the sintered metal is cobalt chrome.

4. The top-loading pedicle screw assembly as defined in claim 1, wherein the open channel in the head is threaded.

5. The top-loading pedicle screw assembly as defined in claim 4, wherein the locking element is a set screw that is dimensioned to expand the outer surface of the head when screwed into the threaded channel to cause the head to forcefully engage and lock to the internal curved socket of the shank top.

6. The top-loading pedicle screw assembly as defined in claim 1, wherein the external curved surface of the head is spherical and the internal curved socket of the shank top is spherical.

7. The top-loading pedicle screw assembly of claim 6, wherein the mating spherical surfaces of the head and shank top are dimensioned to retain the head within the shank top while allowing poly-axial movement therebetween.

8. The top-loading pedicle screw assembly as defined in claim 1, wherein the open channel of the head is generally orthogonal to the through bore of the head.

9. The top-loading pedicle screw assembly as defined in claim 1, further including a flexible clip positioned within the head adapted to receive a rod in a snap fit.

10. The top-loading pedicle screw assembly as defined in claim 9, wherein the locking element forces the head against the clip to further lock the head to the shank top.

11. The top-loading pedicle screw assembly as defined in claim 9, wherein the flexible clip has a pair of ends forming an opening and a rod is dimensioned to enter into and be captured in a snap fit within the flexible clip.

12. The top-loading pedicle screw assembly as defined in claim 1, wherein the head has an angled surface and a slot facing the through bore.

13. The top-loading pedicle screw assembly as defined in claim 1, wherein the locking element and the open channel are dovetail threaded.

14. An orthopedic spinal fusion system comprising:
   at least two top-loading pedicle screw assemblies, each top-loading pedicle screw assembly including:
      a screw having a threaded shaft configured to be secured to a vertebral pedicle,
      a shank top permanently fixed to the screw forming an internal curved socket and including lateral openings, and
      a head having a through bore formed therein, an external curved surface movably fitted within the internal curved socket, an open channel formed therein, the head being configured to allow the rod to be top-loaded into the through bore and the lateral openings of the shank top,
   a rod positioned to pass through the through bore of the at least two top-loading pedicle screw assemblies, and
   a locking element located within the open channel of each head to lock the rod in position within the through bores of the at least two top-loading pedicle screw assemblies.

15. The orthopedic spinal fusion system as defined in claim 14, wherein the open channel in each head is threaded and the locking element is threadedly engaged to the head.

16. The orthopedic spinal fusion system as defined in claim 15, wherein the locking element is a set screw that is dimensioned to expand the external curved surface of the head to cause the head to forcefully engage and lock to the internal curved socket of the shank top.

17. The orthopedic spinal fusion system as defined in claim 14, wherein the open channel is threaded.

18. The orthopedic spinal fusion system as defined in claim 14, wherein the external curved surface of the head is spherical and the internal curved socket of the shank top is spherical.

19. The orthopedic spinal fusion system as defined in claim 14, wherein the open channel is generally orthogonal to the through bore.

20. The orthopedic spinal fusion system as defined in claim 14, further including a flexible clip positioned within the head adapted to receive the rod in a snap fit.

21. The orthopedic spinal fusion system as defined in claim 14, wherein the head has an angled surface and a slot facing the through bore.

22. The orthopedic spinal fusion system as defined in claim 14, wherein the locking element and the open channel are dovetail threaded.

* * * * *